United States Patent [19]

Adelstein et al.

[11] Patent Number: 4,560,754

[45] Date of Patent: Dec. 24, 1985

[54] SUBSTITUTED 5-PHENYL-5-(AMINOALKYL)-1,3-DIAZABICYCLO[4.4.0]DECAN-4-ONES AND 5-PHENYL-5-(AMINOALKYL)-1,3-DIAZABICYCLO[4.4.0]DEC-2-EN-4-ONES

[75] Inventors: Gilbert W. Adelstein, Evanston; Robert J. Chorvat, Arlington Heights, both of Ill.

[73] Assignee: G. D. Searle & Co., Skokie, Ill.

[21] Appl. No.: 635,989

[22] Filed: Jul. 30, 1984

Related U.S. Application Data

[63] Continuation-in-part of Ser. No. 532,120, Sep. 14, 1983, abandoned, which is a continuation-in-part of Ser. No. 424,936, Sep. 27, 1982, abandoned.

[51] Int. Cl.$^4$ .................. C07D 471/04; A61K 31/505
[52] U.S. Cl. .................................... 544/282; 514/258; 260/243.3
[58] Field of Search ......................................... 544/282

[56] References Cited

U.S. PATENT DOCUMENTS 3,515,725  6/1970  Hellerbach ........................... 544/282
4,107,205  8/1978  Renbarger et al. ................. 424/263

FOREIGN PATENT DOCUMENTS 104647   4/1984  European Pat. Off. ............ 544/282
1114397  3/1967  United Kingdom ................ 544/282

Primary Examiner—George F. Lesmes
Assistant Examiner—S. A. Gibson
Attorney, Agent, or Firm—John J. McDonnell

[57] ABSTRACT

This invention relates to 5-(substituted phenyl)-5-[(substituted amino)alkyl]-1,3-diazabicyclo[4.4.0]decan-4-ones and 5-(substituted phenyl)-5-[(substituted amino)-alkyl]-1,3-diazabicyclo[4.4.0]dec-2-en-4-ones that are useful as antiarrhythmic agents.

35 Claims, No Drawings

SUBSTITUTED 5-PHENYL-5-(AMINOALKYL)-1,3-DIAZABICYCLO[4.4.0]DECAN-4-ONES AND 5-PHENYL-5-(AMINOALKYL)-1,3-DIAZABICYCLO[4.4.0]DEC-2-EN-4-ONES

CROSS-REFERENCES

This application is a continuation-in-part of pending application Ser. No. 06/532120 filed Sept. 14, 1983, now abandoned, which is a continuation-in-part of now abandoned application Ser. No. 06/424936 filed Sept. 27, 1982.

BACKGROUND OF THE INVENTION (a) Field of the invention

This invention relates to novel diazabicyclodecanones useful as antiarrhythmic agents. In particular, the invention relates to novel diazabicyclodecanones of the Formulas III and V which are useful in the treatment of arrhythmic disorders.

Arrhythmias are disorders relating to electrical impulse generation in the heart. The disorders include premature contractions (extrasystoles) originating in abnormal or ectopic foci in atria or ventricles, paroxysmal supraventricular tachycardia, atrial flutter, atrial fibrillation, and ventricular tachycardia and fibrillation. For a discussion on these disorders see for example the Pharmacological Basis of Therapeutics, Goodman and Gilman, the MacMillan Co., pgs. 709–711 (1970).

A number of compounds have been developed to alter cardiovascular function related to heart rate and rhythm. The cardiac glycosides, including digitalis, have as their main pharmacodynamic property the ability to increase the force of myocardial contraction. The salutary effects of these cardiac glycosides in congestive heart failure—increased cardiac output, decreased heart size, venous pressure and blood vlume; diuresis and relief of edema—are all explained on the basis of increased contractile force, a positive inotropic action. Quinidine is useful in the therapy of atrial fibrillation but exhibits several toxic reactions, such as cinchonism. The cardiac actions of procainamide are essentially identical to those for quinidine, and like quinidine, procainamide exhibits toxic side effects. Lidocaine, a widely used local anesthetic only administered intravenously may be used in the treatment of ectopic ventricular rhythms, but is not recommended for the treatment of supraventricular arrhythmias. Propranolol has found use in the treatment of supraventricular tachycardias and ventricular arrhythmias but because propranolol antagonizes adrenergic effects on contractility and because serious arrthymias are commonly encountered in the presence of overt or incipient heart failure, the use of the drug for its antiarrhythmic actions demands great care. Disopyramide is similar to procainamide and quinidine (referred to as a Type 1 antiarrhythmics). At therapeutic plasma levels disopyramide shortens the sinus node recovery time, lengthens the effective refractory period of the atrium and has a minimal effect on the effective refractory period of the AV mode. However, because of the anticholinergic effects of some of the Type 1 antiarrhythmics, they should not be used in patients with glaucoma, myasthenia gravis or problems of urinary retention.

(b) Prior Art

As previously described, a number of compounds are useful in the treatment of arrhythmias. The diazabicyclodecanones of the instant invention are novel and represent a new class of compounds useful to treat arrhythmias with reduced anticholinergic activity.

SUMMARY OF THE INVENTION

It is an object of this invention to develop new chemical compounds with reduced anticholinergic activity that are useful in the treatment of arrhythmic conditions.

In accordance with this objective, it has been discovered that compounds of formula:

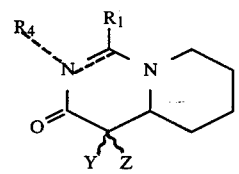

wherein $R_1$ is
(a) hydrogen;
(b) alkyl of from 1 to 6 carbon atoms, inclusive; or
(c)

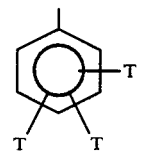

wherein Y is:
(a) hydrogen; or
(b)

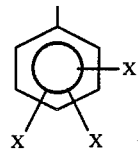

wherein each T is a substituent taken independently, selected from the group consisting of:
(a) hydrogen
(b) halogen;
(c) alkyl of from 1 to 6 carbon atoms, inclusive;
(d) alkoxy of from 1 to 6 carbon atoms, inclusive; or
(e) phenyl;
wherein each X is a substituent taken independently, selected from the group consisting of:
(a) hydrogen;
(b) halogen;
(c) alkyl of from 1 to 6 carbon atoms, inclusive;
(d) alkoxy of from 1 to 6 carbon atoms, inclusive; or
(e) phenyl;
wherein Z is:
(a) hydrogen; or
(b) —$(CH_2)_n$—$NR_2R_3$, wherein n is 1 to 6;
wherein $R_2$ and $R_3$ are:
(a) alkyl of from 1 to 6 carbon atoms, inclusive, $R_2$ and $R_3$ each being the same or different; or wherein $R_2$ and $R_3$ are taken together to form a cyclic structure either saturated or unsaturated of from 4 to 6 carbon atoms, inclusive;

wherein R₄ is:
(a) hydrogen; or
(b) alkyl 1 to 6 carbon atoms, inclusive; with the proviso that R₄ is present only where the adjacent ring nitrogen atom is not doubly bonded in the optional ring double bond;
and the pharmacologically acceptable salts are useful for their antiarrhythmic activity and exhibit reduced anticholinergic activity.

Examples of alkyl of from 1 to 6, inclusive, are methyl, ethyl, propyl, butyl, pentyl, hexyl and isomeric forms thereof.

Examples of halogen are chloro and bromo.

Examples of alkoxy of from 1 to 6 carbon atoms, inclusive are methoxy, ethoxy, propoxy, butoxy, pentoxy, hexoxy and isomeric forms thereof.

Examples of saturated nitrogen-containing cyclic structures of 5 to 7 atoms, inclusive, are 1-azacyclopentyl, 1-azacyclohexyl and 1-azacycloheptyl.

Examples of unsaturated nitrogen-containing cyclic structures of 5 to 7 atoms, inclusive, are 1-pyrrolinyl, 1-pyrrolyl, 1-dihydropyridinyl, 1-tetrahydropyridinyl, 1-azacycloheptenyl, 1-azacycloheptadienyl, 1-azepinyl.

Antiarrhythmic activity was confirmed using ventricular arrhythmia induced in unanesthetized dogs. Ventricular arrhythmia is induced by a two-stage ligation of the anterior descending branch of the left coronary artery in each of two or more dogs. A test compound is rated active if it produces at least a 25% reduction in ectopic beats for a period of at least 10 minutes in half or more of the dogs tested. An active compound may act by suppressing the ectopic pacemaker, thus allowing normal sinus rhythm to return. This arrhythmia is considered similar in nature to the arrhythmia resulting from myocardial infarction in man. Quinidine and procainamide are active in this test and are effective in man.

By virtue of the antiarrhythmic activity, the compounds of Formulas III and V are useful in treating arrhythmias in mammals. A physician or veterinarian of ordinary skill could readily determine a subject who exhibits arrhythmias.

Regardless of the route of administration selected, the compounds of the present invention are formulated into pharmaceutically acceptable dosage forms by conventional methods known to those familiar with the pharmaceutical art.

The compounds can be administered in such oral unit dosage forms as tablets, capsules, pills, powders, or granules. They also may be administered intraperitoneally, subcutaneously, or intramuscularly, using forms known to those familiar with the pharmaceutical art. In general, the preferred form of administration is oral.

An effective but non-toxic quantity of the compound is employed in treatment. The dosage regimen for preventing or treating arrhythmia by the compounds of this invention is selected in accordance with a variety of factors including the type, age, weight, sex, and medical condition of the patient, the severity of the arrhythmia, the route of administration and the particular compound employed. An ordinarily skilled physician or veterinarian will readily determine and prescribe the effective amount of the antiarrhythmic agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 1.0 mg/kg up to at least 10.0 mg/kg orally.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention are prepared according to the general scheme on Chart A from the available racemic butanamides, I.

CHART A

Reduction of the pyridine ring of I, in which a new chiral center is formed, gives a mixture of four diastereomers, II. This may be accomplished by catalytic hydrogenation using catalysts such as Raney nickel, platinum, palladium or the like, or reaction with an alkali metal, such as sodium or lithium, in ammonia. The mixture of four compounds can be separated, for example by crystallization, into two racemates before further reactions are performed. In general, as can be expected for racemates, each racemic pair exhibits distinct and reproducible physical properties such as melting point and NMR spectra, and each racemate can be distinguished from the other by these and other properties.

CHART A

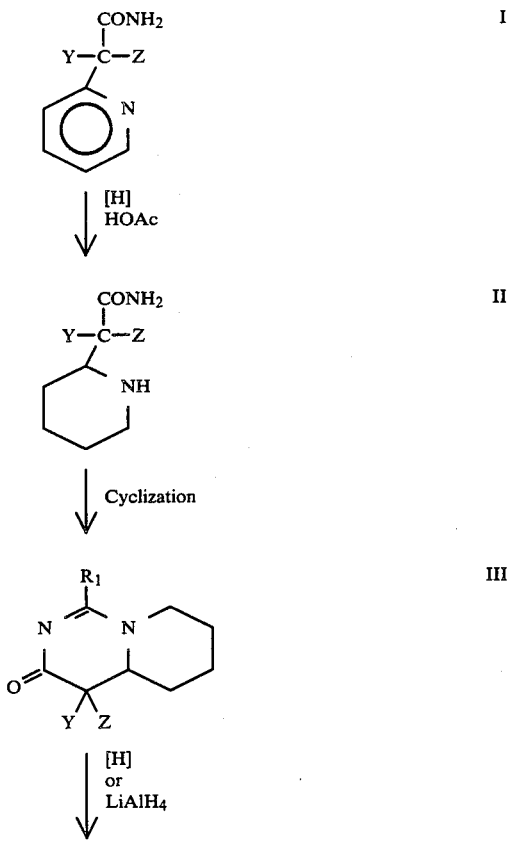

-continued
CHART A

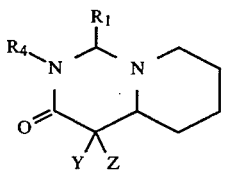

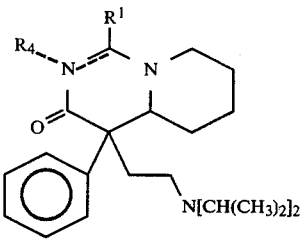

The intermediate compounds II are cyclized to corresponding diazabicyclic compounds III, for example by reaction with a dialkyl ketal or acetal of an amide, with an orthoester, or with other reactive formyl equivalents. Examples of amides which can be used as their ketals or acetals include dimethylformamide, dimethylacetamide, and dimethylbenzamide. Examples of orthoesters include triethylorthoformate, triethylorthoacetate, and triethylorthobenzoate. Examples of other reactive formyl equivalents include bis(dimethylamino)methoxymethane and tris(dimethylamino)methane. The preferred method of cyclization involves an initial acylation of the ring nitrogen atom of compounds of Formula II, followed by base-induced ring closure. Preferred acylating reagents include acid anhydrides, such as acetic anhydride, propanoic anhydride, benzoic anhydride, and the like. Preferred conditions for ring closure include alkali metal hydroxides, such as sodium hydroxide, in strongly polar organic solvents, such as dimethylsulfoxide and methanol.

These bicyclic compounds can in turn be converted to compounds V by reductive procedures, for example catalytic hydrogenation, using Raney nickel, platinum, palladium or the like, or reaction with an active metal hydride such as lithium aluminum hydride, sodium borohydride, or one of the available derivative variations of these reagents. Compounds of Formula V in which $R_4$ is lower alkyl can, for example, be prepared by the alkylation method described in Example 24.

The preferred embodiments of this invention include compounds of the formula general structure, Formula VI.

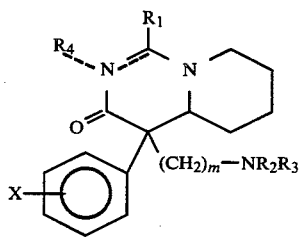

More specifically, the preferred embodiments include compounds of Formula VI wherein $R_1$ is hydrogen, lower alkyl (that is, consisting of 1 to 6 carbon atoms, inclusive), or phenyl; wherein $R_2$ and $R_3$ are lower alkyl; wherein $R_4$ is hydrogen, with the proviso that $R_4$ is present only when the adjacent ring nitrogen atom is not double bonded in the optional ring double bond; and wherein X is hydrogen, halogen, or phenyl.

The most preferred embodiments of this invention include compounds of the following general structure, Formula VII.

More specifically, the most preferred embodiments include compounds of Formula VII wherein $R_1$ is hydrogen, lower alkyl (that is, consisting of 1 to 6 carbon atoms, inclusive), or phenyl; and wherein $R_4$ is hydrogen, with the proviso that $R_4$ is present only when the adjacent ring nitrogen atom is not doubly bonded in the optional ring double bond.

The following examples further illustrate details for the preparation and testing of the compounds and salts of the invention. The invention, which is fully set forth in the foregoing disclosure, is not to be construed as being limited either in spirit or scope by these examples. Those skilled in the art will readily understand that known variations of the conditions and processes of the following preparative procedures can also be used to prepare the compounds of the invention. All temperatures are in degrees celsius unless otherwise noted.

DESCRIPTION OF THE PREFERRED EMBODIMENTS

EXAMPLE 1

Preparation of 2-phenyl-2-(2-piperidinyl)-4-[N,N-bis(1-methylethyl)amino]butanamide, Racemate A(II).

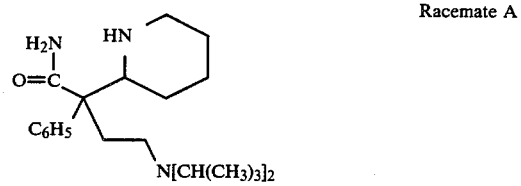

Racemate A

A mixture of 105.3 g (0.31 mole) of racemic 2-phenyl-2-(2-pyridyl)-4-[N,N-bis(1-methylethyl)amino]butanamide and 27 ml (ca. 0.32 mole) of concentrated aqueous hydrochloric acid in 2.5 liters of ethanol was hydrogenated (50 psi) over platinum oxide catalyst. After filtration to remove the catalyst, the reaction mixture was reduced to a syrupy residue, dissolved in an ice/water mixture, and neutralized with a slight excess of 25% sodium hydroxide. The product mixture was extracted into diethyl ether, which was dried over magnesium sulfate, filtered, and concentrated to dryness. The crude product was crystallized twice from Skellysolve B containing a small amount of diethyl ether, to yield 26.0 g of the title compound as a white solid, m.p. 107°–108°. Structure assignment was confirmed by proton and carbon-13 NMR spectra and by elemental analysis.

H—NMR(CDCl$_3$)δppm 0.83, 0.92, 7.33

EXAMPLE 2

Preparation of a 2-phenyl-2-(2-piperidinyl)-4-[N,N-bis(1-methylethyl)amino]butanamide, Racemate B(II).

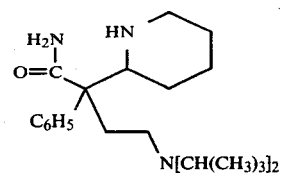

Racemate B

The final filtrate from Example 1 was concentrated under a stream of nitrogen to an oil which slowly solidified. The crude material was chromatrographed several times on silica gel to yield a total of 17 g of the title compound as a white solid, m.p. 81°–82°. Structure assignment was confirmed by proton and carbon-13 NMR spectra and by elemental analysis.

H—NMR(CDCl$_3$)δppm 0.96, 1.05, 7.30

EXAMPLE 3

An alternative preparation of 2-phenyl-2-(2-piperidinyl)-4-[N,N-bis(1-methylethyl)amino]butanamide. The compounds of Examples 1 and 2 were prepared by hydrogenation in the same manner as in Example 1, except that about 1.3 l of acetic acid was used as solvent and no hydrochloric acid was added.

EXAMPLE 4

Preparation of 5-phenyl-5-[2-[N,N-bis-(1-methylethyl)-amino]ethyl]-1,3-diazabicyclo[4.4.0]-dec-2-en-4-one, Racemate A(III).

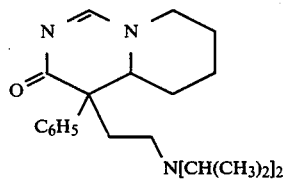

Racemate A

A solution of 16.35 g (47 mmole) of Racemate A(II) (of Example 1) and 8.9 g (60 mole) of dimethylformamide diethyl acetal in 100 ml of dimethylformamide was stirred overnight under nitrogen at room temperature. Water was added, and the resultant precipitate was collected, washed thoroughly with water, and dried, yielding 12.9 g of the title compound as a white solid. Structure assignment was supported by NMR and by elemental analysis.

|  | C | H | N | Characteristic Peaks |
|---|---|---|---|---|
| Calc'd | 74.33 | 9.36 | 11.82 | NMR(CDCl$_3$) δppm 0.77, 0.82, 0.85, 0.90, 7.18, 7.25 |
| Fd. | 74.27 | 9.51 | 11.91 | IR(CHCl$_3$) 2980, 1685, 1580 cm$^{-1}$ UV(MeOH) λmax 274–5 nm |

EXAMPLE 5

Preparation of 5-phenyl-5-[2-[N,N-bis(1-methylethyl)amino]ethyl]-1,3-diazabicyclo[4.4.0]-decan-4-one, Racemate A(V).

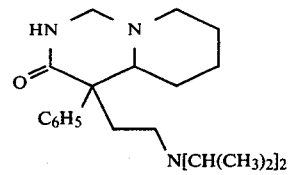

Racemate A

A solution of 14.0 g (39.4 mmole) of Racemate A(III), prepared by the method of Example 4, in 260 ml of ethanol was hydrogenated (5 psi) over 5% palladium on carbon. After the catalyst was removed by filtration, the solvent was removed from the filtrate to give a white solid. Recrystallization from ethyl acetate afforded 10.0 g of the title compound, m.p. 204°–206°. Structure assignment was confirmed by proton and carbon-13 NMR and infrared spectra and by elemental analysis.

|  | C | H | N |  |
|---|---|---|---|---|
| Calc'd | 73.91 | 9.87 | 11.75 | NMR(CDCl$_3$) δppm 1.03, 1.06, 1.12, 1.15, 7.15 |
| Fd | 73.90 | 9.71 | 11.83 | IR(CHCl$_3$) 3410, 2985, 1680 cm$^{-1}$ |

EXAMPLE 6

Preparation of 5-phenyl-5-[2-[N,N-bis(1-methylethyl)amino]ethyl]-1,3-diazabicyclo[4.4.0]-dec-2-en-4-one, Racemate B(III).

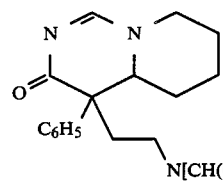

Racemate B

The title compound was prepared by the method of Example 4 using 1.7 g (4.9 mmole) of Racemate B(II) (of Example 2) and 1.0 g of dimethylformamide diethyl acetal in 12 ml of dimethylformamide. After one day the solution was concentrated to dryness in vacuo. The residue was recrystallized from diethyl ether to give the title compound as a white solid, m.p. 155°–158°. Structure assignment was confirmed by proton NMR, ultraviolet, and infrared spectra and by elemental analysis.

|  | C | H | N |  |
|---|---|---|---|---|
| Calc'd. | 74.33 | 9.36 | 11.82 | NMR(CDCl$_3$) δppm 0.80, 0.82, 0.89, 0.91, 7.29 |
| Fd. | 74.22 | 9.53 | 11.84 | UV(MeOH) λmax 273–274 nm IR(CHCl$_3$) 2980, 1680, 1585 cm$^{-1}$ |

EXAMPLE 7

Preparation of 5-phenyl-5-[2-[N,N-bis(1-methylethyl)amino]ethyl]-1,3-diazabicyclo[4.4.0]decan-4-one, Racemate B(V).

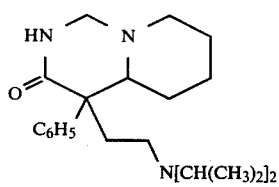

Racemate B

The title compound was prepared by the method of Example 5 using 200 mg (0.56 mmole) of Racemate B(III) (of Example 6). The reaction mixture was concentrated to dryness and the residue was triturated with diethyl ether. The structure of the product, a white solid (0.18 g), was confirmed by proton NMR, infrared, and ultraviolet spectra and by elemental analysis, m.p. 164°–166°.

|  | C | H | N |  |
|---|---|---|---|---|
| Calc'd | 73.91 | 9.87 | 11.75 | NMR(CDCl$_3$) δppm 1.00, 1.10, 7.05, 7.55 |
| Fd. | 74.00 | 9.85 | 11.65 |  |

EXAMPLE 8

Preparation of 2-methyl-5-phenyl-5-[2-[N,N-bis-(1-methylethyl)amino]ethyl]-1,3-diazabicyclo[4.4.0]dec-2-en-4-one, Racemate A(III, $R_1$=methyl).

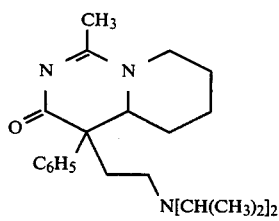

Racemate A

A mixture of 20.0 g (57.0 mmole) of Racemate A(II) (of Example 1) and 22.0 g (165 mmole) of N,N-dimethylacetamide dimethyl acetal was heated at 80° for about 14 hours. After cooling, the reaction mixture was diluted with diethyl ether, filtered, washed with diethyl ether, and air-dried, giving 6.0 g of the title compound, m.p. 191°–192°. The product had the expected elemental composition.

|  | C | H | N |  |
|---|---|---|---|---|
| Calc'd | 74.75 | 9.55 | 11.37 | NMR(CDCl$_3$) δppm 0.77, 0.80, 0.87, 0.90, 1.95, m 7.23 |
| Fd | 74.49 | 9.57 | 11.39 | IR(CHCl$_3$) 2970, 1675, 1540, 1480 cm$^{-1}$ |
|  |  |  |  | UV(MeOH) λmax 273.274 nm |

EXAMPLE 9

Preparation of 2-methyl-5-phenyl-5-[2-N,N-bis-(1-methylethyl)amino]ethyl]-1,3-diazabicyclo[4.4.0]dec-2-en-4-one, Racemate B(III, $R_1$=methyl).

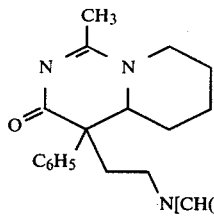

Racemate B

The title racemate is prepared by the method of Example 8 using Racemate B(II) (of Example 2).

EXAMPLE 10

Preparation of 2-methyl-5-phenyl-5-[2-[N,N-bis(1-methylethyl)amino]ethyl]-1,3-diazabicyclo[4.4.0]-decan-4-one, Racemate A'(V, $R_1$=methyl).

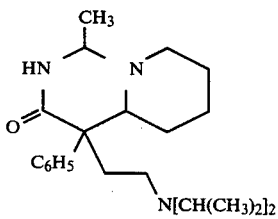

Racemate A'

To a solution of 2.8 g (7.6 mmole) of Racemate A(III, $R_1$=methyl) (of Example 8) in 40 ml of freshly distilled tetrahydrofuran was added, in portions, 0.57 g (15.0 mmole) of lithium aluminum hydride. The mixture was stirred at ambient temperature for two hours and then cooled in an ice bath. The reaction was quenched by adding 1.2 ml of water, 1.2 ml of 15% aqueous sodium hydroxide, and another 3.0 ml of water, and the resulting precipitate was removed by filtration. The filtrate was concentrated to dryness, and the residue dried in vacuo at about 50° for 12 to 15 hours, giving 2.4 g of the title compound as a white solid, m.p. 70°–75°. Structure assignment was confirmed by porton NMR and infrared spectra and by elemental analysis.

|  | C | H | N |  |
|---|---|---|---|---|
| Calc'd. | 74.35 | 10.04 | 11.31 | NMR(CDCl$_3$) δppm 0.99, 1.01, 1.08, 1.10, 1.28, 1.35, 7.50 |
| Fd. | 74.36 | 9.95 | 11.34 | IR(CHCl$_3$) 3400, 2985, 1665 cm$^{-1}$ |

EXAMPLE 11

Preparation of 2-methyl-5-phenyl-5-[2-N,N-bis-(1-methylethyl)amino]ethyl]-1,3-diazabicyclo[4.4.0]-decan-4-one, Racemate B'(V, $R_1$=methyl).

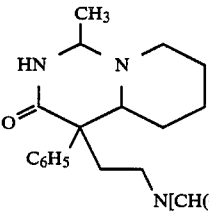

Racemate B'

The title racemate is prepared by the method of Example 10 using Racemate B(III) (of Example 9).

EXAMPLE 12

Preparation of racemic 2-(4-phenylphenyl)-2-(2-pyridyl)-4-[N,N-bis(1-methylethyl)amino]butanenitrile.

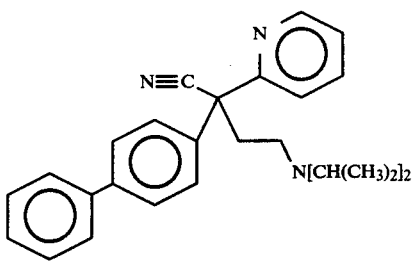

A mixture of 50.0 g (0.16 mole) of 2-(4-phenylphenyl)-4-[N,N-bis(1-methylethyl)amino]butanenitrile and 29.7 g of potassium hydride (about 0.26 mole as a 35% dispersion in oil) in 1000 ml of toluene was heated at 65°. A solution of 32 g (0.20 mole) of 2-bromopyridine in 450 ml of toluene was added slowly. After addition was complete, the mixture was stirred an additional 30 minutes, cooled in an ice bath, and treated with 750 ml of water. The toluene layer was separated and extracted with 10% aqueous hydrochloric acid. The acidic aqueous layer was neutralized with a slight excess of aqueous sodium hydroxide and extracted wih dichloromethane. The organic phase was washed with brine, dried over magnesium sulfate, filtered, and concentrated to dryness, giving 56.5 g of the title compound as an oil having the expected NMR spectrum. The intermediate nitrile was used without further purification.

EXAMPLE 13

Preparation of racemic 2-(4-phenylphenyl)-2-(2-pyridyl)-4-[N,N-bis(1-methylethyl)amino]butanamide.

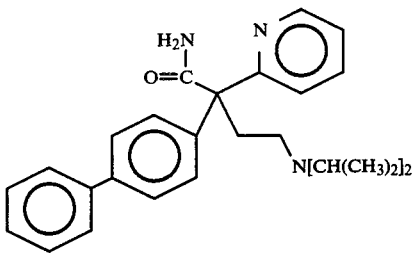

A mixture of 1.0 g (2.5 mmole) of the nitrile from Example 12 and 2 g of powdered potassium hydroxide in 10 ml of t-butyl alcohol was heated at reflux for about 12 hours. After cooling, the reaction mixture was treated with water and extracted with diethyl ether. The organic phase was dried over magnesium sulfate, filtered, and concentrated to an oil. Crystallization from Skellysolve B afforded the title compound (0.46 g) as a white solid. Structure assignment was supported by proton NMR and infrared spectra and by elemental analysis.

|  | C | H | N |  |
|---|---|---|---|---|
| Calc'd. | 78.04 | 8.00 | 10.11 | NMR(CDCl$_3$) δppm 0.88, 0.95, 7.0–7.75, 8.50, 8.55 |
| Fd. | 77.92 | 8.06 | 9.88 | IR(CHCl$_3$) 3350, 2970, 1670 cm$^{-1}$ |

EXAMPLE 14

Preparation of 5-(4-phenylphenyl)-5-[2-[N,N-bis(1-methylethyl)amino]ethyl]-1,3-diazabicyclo[4.4.0]-dec-2-en-4-one, Racemate C(III, X=phenyl).

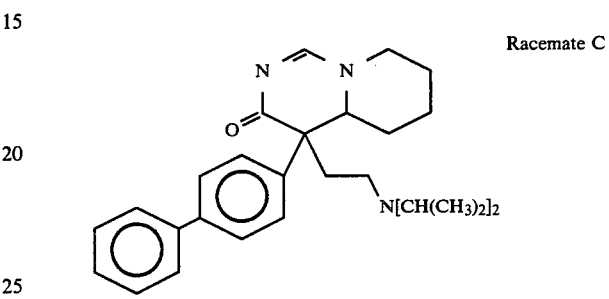

Racemate C

The title racemate, m.p. 257°–258°, was prepared by the methods of Examples 1 and 4 using the racemic amide of Example 13. Structure assignment was supported by nmr and infrared spectra and by elemental analysis.

|  | C | H | N |  |
|---|---|---|---|---|
| Calc'd. | 77.92 | 8.64 | 9.73 | NMR(CDCl$_3$) δppm 0.79, 0.85, 0.88, 0.94, 7.05–7.65 |
| Fd. | 77.93 | 8.79 | 9.74 | IR(CHCl$_3$) 2985, 1680, 1575 cm$^{-1}$ |

EXAMPLE 15

Preparation of 5-(4-phenylphenyl)-5-[2-[N,N-bis(1-methylethyl)amino]ethyl]-1,3-diazabicyclo[4.4.0]dec-2-en-4-one, Racemate D(III, X=phenyl).

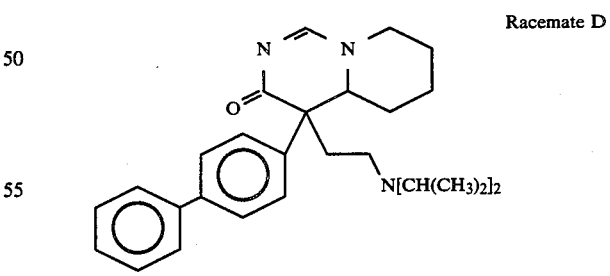

Racemate D

The title racemate is prepared by the methods of Examples 2 and 4 using the racemic amide of Example 13.

EXAMPLE 16

Preparation of 5-(4-phenylphenyl)-5-[2-[N,N-bis(1-methylethyl)amino]ethyl]-1,3-diazabicyclo[4.4.0]decan-4-one, Racemate C(V, X=phenyl).

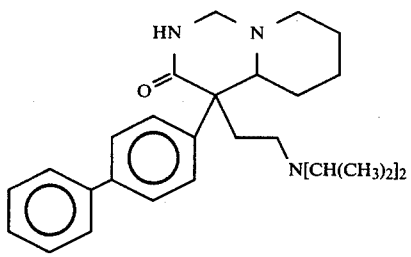

Racemate C

The title racemate was prepared by the method of Example 5 using Racemate C(III, X=phenyl) (of Example 14). Structure assignment was supported by the nmr, infrared, and ultraviolet spectra and by elemental analysis.

|  | C | H | N |  |
|---|---|---|---|---|
| Calc'd. | 77.56 | 9.06 | 9.65 | NMR(CDCl₃) δppm 1.02, 1.05, 1.10, 1.13, 7.05–7.65 |
| Fd | 77.11 | 9.03 | 9.74 | IR(CHCl₃) 3400, 2960, 1660 cm⁻¹ UV(MeOH) λmax 254 mm |

EXAMPLE 17

Preparation of 5-(4-phenylphenyl-5-[2-[N,N-bis(1-methylethyl)amino]ethyl]-1,3-diazabicyclo[4.4.0]decan-4-one, Racemate D(V, X=phenyl).

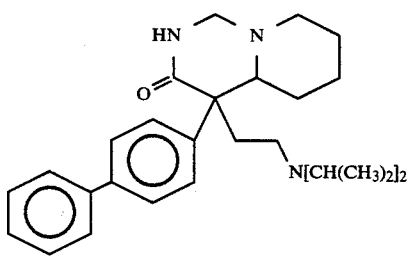

Racemate D

The title racemate is prepared by the method of Example 5 using Racemate D(III, X=phenyl) (of Example 15).

EXAMPLE 18

Preparation of 5-(2-chlorophenyl)-5-[2-[N,N-bis(1-methylethyl)amino]ethyl]-1,3-diazabicyclo[4.4.0]dec-2-en-4-one, Racemate E(III, X=chloro).

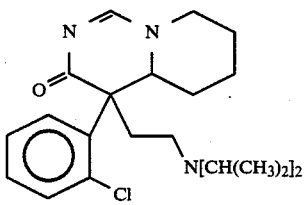

Racemate E

The title racemate, m.p. 154°–156°, was prepared by the methods of Example 1 and 4 using 28.5 g (76 mmole) of racemic 2-(2-chlorophenyl)-2-(2-pyridyl)-4-[N,N-bis(1-methylethyl)amino]butanamide.

|  | C | H | N | Cl |  |
|---|---|---|---|---|---|
| Calc'd. | 67.76 | 8.27 | 10.78 | 9.09 | NMR(CDCl₃) δppm 0.90, 0.95, 0.98, 1.03, 7.05–7.45 |
| Fd. | 67.90 | 8.28 | 10.54 | 9.10 | IR(CHCl₃) 2960, 1680, 1580 cm⁻¹ UV(MeOH) λmax 273–4 nm |

EXAMPLE 19

Preparation of 5-(2-chlorophenyl)-5-[N,N-bis(1-methylethyl)amino]ethyl]-1,3-diazabicyclo]4.4.0]dec-2-en-4-one, Racemate F(III, X=chloro).

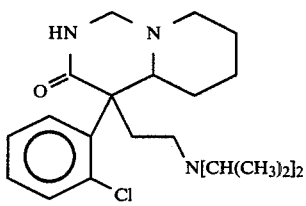

Racemate F

The title racemate is prepared by the methods of Examples 2 and 4 using racemic 2-(2-chlorophenyl)-2-(2-pyridyl)-4-[N,N-bis(1-methylethyl)amino]butanamide.

EXAMPLE 20

Preparation of 5-(2-chlorophenyl)-5-[2-[N,N-bis(1-methylethyl)amino]ethyl]-1,3-diazabicyclo[4.4.0]decan-4-one, Racemate E(V, X=chloro).

Racemate E

The title racemate, m.p. 232°–235°, was prepared by the method of Example 10 using Racemate E(III, X=chloro) (of Example 18). Structure assignment was supported by nmr, infrared, and ultraviolet spectra and by elemental analysis.

|  | C | H | N | Cl |  |
|---|---|---|---|---|---|
| Calc'd. | 67.41 | 8.74 | 10.72 | 9.04 | NMR(CDCl₃) δppm 1.01, 1.09, 7.05–7.65 |
| Fd. | 67.46 | 8.93 | 10.40 | 8.76 | IR(CHCl₃) 3410, 2970, 1670 cm⁻¹ |

EXAMPLE 21

Preparation of 5-(2-chlorophenyl)-5-[2-[N,N-bis(1-methylethyl)amino]ethyl]-1,3-diazabicyclo[4.4.0]decan-4-one, Racemate F(V, X=chloro).

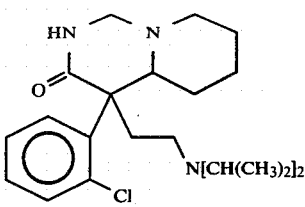

Racemate F

The title racemate is prepared by the method of Example 10 using Racemate F(III, X=chloro) (of Example 19).

EXAMPLE 22

Preferred preparation of 2-methyl-5-phenyl-5-[2-[N,N-bis(1-methylethyl)amino]ethyl]-1,3-diazabicyclo-[4.4.0]dec-2-en-4-one, Racemate A(III, $R_1$=methyl).

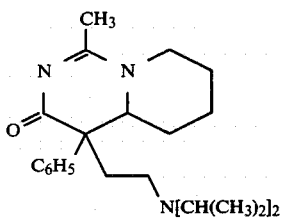

Racemate A

A mixture of 4.2 kg (12 moles) of Racemate A(II) (of Example 1) and 9.7 liters (103 moles) of acetic anhydride was stirred under dry nitrogen at room temperature for 23 hours. After diluting with 13 liters of dichloromethane, the reaction mixture was added with stirring to 75 liters of 3M ammonium hydroxide cooled to 10°. After one hour the mixture was allowed to separate into layers. The organic layer was separated and the aqueous layer was extracted with dichloromethane. The combined organic layers were then washed with water, dried over sodium sulfate, filtered, and concentrated in vacuo to dryness, giving the acetylated intermediate. A mixture of the acetyl intermediate and 0.8 kg (12 moles) of powdered sodium hydroxide in 15 liters of dimethylsulfoxide was stirred under dry nitrogen at room temperature for two hours. Approximately 20 liters of dichloromethane and 85 liters of water were then added, and the mixture was stirred for thirty minutes. As before, the organic layer was separated and the aqueous layer was extracted with dichloromethane. The combined organic layers were then washed with water, dried over sodium sulfate, filtered, and concentrated in vacuo to dryness. The residue was dissolved in 15 liters of refluxing toluene. After cooling below 60°, the solution was diluted with 15 liters of heptane and allowed to cool to 10°. The title compound, m.p. 195.5°–197°, was collected in two crops. Elemental analysis and infrared and NMR spectra indicated that the title compound was the same as that prepared by the method of Example 8.

EXAMPLE 23

TABLE 1

Preparation of Substituted 1,3-Diazabicyclo-[4.4.0]dec-2-en-4-ones.

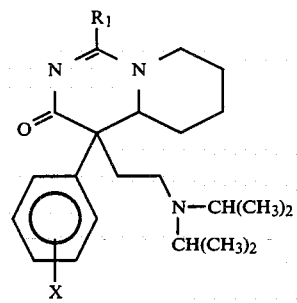

| X | $R_1$ | Racemate | Examples for Methods Used* | Example for Amide Precursor (II) |
|---|---|---|---|---|
| H | Ethyl | A | 22 | 1 |
| H | Ethyl | B | 22 | 2 |
| H | Phenyl | G | 22 | 1 |
| H | Phenyl | H | 22 | 2 |
| 4-Phenyl | Methyl | K | 4, 8, or 22 | 13 |
| 4-Phenyl | Methyl | L | 6, 9, or 22 | 13 |
| 4-Phenyl | Phenyl | M | 4, 8, or 22 | 13 |
| 4-Phenyl | Phenyl | N | 6, 9, or 22 | 13 |
| 2-Chloro | Methyl | P | 4, 8, or 22 | # |
| 2-Chloro | Methyl | Q | 6, 9, or 22 | # |
| 2-Chloro | Phenyl | R | 4, 8, or 22 | # |
| 2-Chloro | Phenyl | S | 6, 9, or 22 | # |

*All methods other than for "Ex. 22" require use of dialkyl ketal of appropriate amide $R_1$—CON(Alkyl)$_2$. Variations on the syntheses use similar orthoesters or active methylene compounds of general type $R_1$—$CX_3$, where X=OAlkyl, N(Alkyl)$_2$ (or combinations thereof), and the like.
Precursor: 2-(2-chlorophenyl)-2-(2-pyridyl)-4-[N,N—bis(1-methylethyl)amino]-butanamide.

EXAMPLE 24

TABLE 2

Preparation of Substituted 1,3-Diazabicyclo-[4.4.0]decan-4-ones from compounds of Table 1.

| X | $R_1$ | Racemate | Examples for Methods Used |
|---|---|---|---|
| H | Ethyl | A' | 5 or 10 |
| H | Ethyl | B' | 7 or 11 |
| H | Phenyl | G' | 5 or 10 |
| H | Phenyl | H' | 7 or 11 |
| 4-Phenyl | Methyl | K' | 5 or 10 |
| 4-Phenyl | Methyl | L' | 7 or 11 |
| 4-Phenyl | Phenyl | M' | 5 or 10 |
| 4-Phenyl | Phenyl | N' | 7 or 11 |
| 2-Chloro | Methyl | P' | 5 or 10 |
| 2-Chloro | Methyl | Q' | 7 or 11 |
| 2-Chloro | Phenyl | R' | 5 or 10 |
| 2-Chloro | Phenyl | S' | 7 or 11 |

EXAMPLE 25

Preparation of 3-methyl-5-phenyl-5-[2-[N,N-bis(1-methylethyl)amino]ethyl]-1,3-diazabicyclo[4.4.0]-decan-4-one, Racemate A (V, $R_4$=methyl)

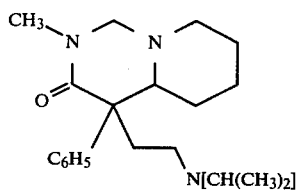

Racemate A

To 0.26 g (5.5 mmoles) of 50% sodium hydride mineral oil dispersion (previously washed with Skellysolve B to remove the mineral oil) in 25 ml of DMF was added 1.63 g (4.6 mmoles) of Racemate A of Example 5 and the reaction mixture was stirred at room temperature for 15 minutes. After this time 0.97 g (6.8 mmoles) of methyl iodide was added to the reaction mixture, which was stirred for an additional 40 min. The excess sodium hydride was then destroyed with $H_2O$ before partitioning the reaction mixture between $H_2O$ and ether/ethyl acetate(1:1 by volume). The organic phase was extracted 3 times with 1N HCl solution and the acidic solution was backwashed one with ether. The aqueous acidic solution was made basic with 5% sodium hydroxide solution and extracted with ether. The ether extracts were dried over sodium sulfate. Solvent removal gave an oil which upon chromatography over silica gel (using $CHCl_3$/EtOH/$NH_4OH$ as the eluent) afforded pure title compound as an oil.

|        | C     | H     | N     |
|--------|-------|-------|-------|
| Calc'd | 74.35 | 10.04 | 11.31 |
| Fd.    | 74.35 | 10.22 | 10.80 |

NMR(CDCl$_3$) δppm 100, 1.10, 3.03, 7.17–7.33; IR (CHCl$_3$) 1650 cm$^{-1}$.

EXAMPLE 26

Preparation of 2-methyl-5-phenyl-5-[2-[N,N-bis(1-methylethyl)amino]ethyl]-1,3-diazabicyclo[4.4.0]decan-4-one.

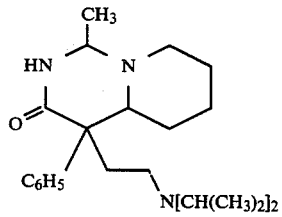

To 2.29 g (12 mmoles) of cuprous iodide in 20 ml of dry tetrahydrafuran (THF) cooled to ca. −20° C. in an argon atmosphere was added dropwise 8.3 ml of 2.9M methyl magnesium chloride/THF (24 mmoles). After stirring for 10 minutes, 2.84 g (8 mmoles) of Racemate A of Example 4 in 60 ml of THF was added dropwise at the above temperature. After addition the reaction mixture was stirred for an additional hour, allowed to warm to room temperature, and stirred for another hour. After cooling to 0° C. 1N HCl solution was added until the solution attained a pH of 3. After stirring for 30 minutes, the solution was made basic (pH 12) with a potassium hydroxide solution and the two layers were separated. The aqueous phase was extracted with additional portions of ether and the combined extracts were washed three times with 3% NH$_4$OH solution followed by saturated sodium chloride solution. The solution was then dried over sodium sulfate and upon solvent removal a pale yellow solid remained. Chromatography of this residue over silica gel using CH$_2$Cl$_2$/EtOH/NH$_4$OH (85:14:1 by volume) as an eluent afforded the pure title compound, m.p. 142°–145° C., in which the 2-methyl group has the opposite sterochemical orientation from that of the title compound of Example 10.

|        | C     | H     | N     |
|--------|-------|-------|-------|
| Calc'd | 74.35 | 10.04 | 11.31 |
| Fd.    | 73.97 | 10.05 | 11.22 |

NMR(CDCl$_3$) δppm 0.85, 0.87, 0.94, 0.96, 1.08, 1.14, IR (CHCl$_3$) 3400, 1665 cm$^{-1}$.

We claim:

1. A compound of the Formula:

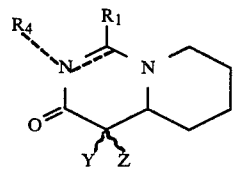

wherein $R_1$ is:
(a) hydrogen;
(b) alkyl of from 1 to 6 carbon atoms, inclusive: or
(c)

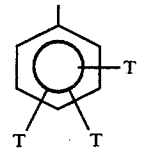

wherein Y is:

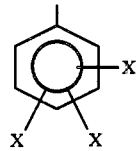

wherein each T is a substituent taken independently, selected from the group consisting of:
(a) hydrogen;
(b) halogen;
(c) alkyl of from 1 to 6 carbon atoms, inclusive;
(d) alkoxy of from 1 to 6 carbon atoms, inclusive; or
(e) phenyl;

wherein each X is a substituent taken independently, selected from the group consisting of:
(a) hydrogen;
(b) halogen;
(c) alkyl of from 1 to 6 carbon atoms, inclusive;

(d) alkoxy of from 1 to 6 carbon atoms, inclusive; or (e) phenyl;

wherein Z is —(CH$_2$)$_n$—NR$_2$R$_3$, wherein n is 1 to 6; wherein R$_2$ and R$_3$ are alkyl of from 1 to 6 carbon atoms, inclusive, R$_2$ and R$_3$ each being the same or different;

wherein R$_4$ is:

(a) hydrogen; or (b) alkyl of 1 to 6 carbon atoms, inclusive; with the proviso that R$_4$ is present only where the adjacent ring nitrogen atom is not doubly bonded in the optional ring double bond; or the pharmacologically acceptable salts.

2. A compound according to claim 1 having the formula:

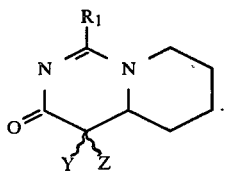

3. A compound according to claim 2 having the formula:

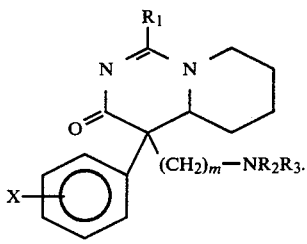

4. A compound according to claim 3 having the formula:

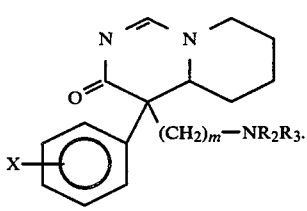

5. 5-phenyl-5-[2-[N,N-bis(1-methylethyl)amino]ethyl]-1,3-diazabicyclo[4.4.0]dec-2-en-4-one, and the corresponding isomers and racemates thereof, compounds according to claim 4.

6. 5-(4-phenylphenyl)-5-[2-[N,N-bis(1-methylethyl)amino]ethyl]-1,3-diazabicyclo[4.4.0]dec-2-en-4-one, and the corresponding isomers and racemates thereof, compounds according to claim 4.

7. 5-(2-chlorophenyl)-5-[2-[N,N-bis(1-methylethyl)amino]ethyl]-1,3-diazabicyclo[4.4.0]dec-2-en-4-one, and the corresponding isomers and racemates thereof, compounds according to claim 4.

8. A compound according to claim 3 having the formula:

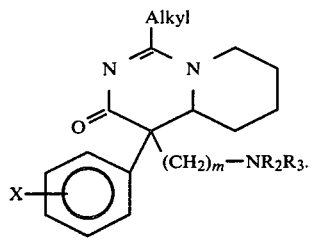

9. 2-methyl-5-phenyl-5-[2-[N,N-bis(1-methylethyl)amino]ethyl]-1,3-diazabicyclo[4.4.0]dec-2-en-4-one, and the corresponding isomers and racemates thereof, compounds according to claim 8.

10. 2-ethyl-5-phenyl-5-[2-[N,N-bis(1-methylethyl)amino]ethyl]-1,3-diazabicyclo[4.4.0]dec-2-en-4-one, and the corresponding isomers and racemates thereof, compounds according to claim 8.

11. 2-methyl-5-(4-phenylphenyl)-5-[2-[N,N-bis(1-methylethyl)amino]ethyl]-1,3-diazabicyclo[4.4.0]dec-2-en-4-one, and the corresponding isomers and racemates thereof, compounds according to claim 8.

12. 2-methyl-5-(2-chlorophenyl)-5-[2-[N,N-bis(1-methylethyl)amino]ethyl]-1,3-diazabicyclo[4.4.0]dec-2-en-4-one, and the corresponding isomers and racemates thereof, compounds according to claim 8.

13. A compound according to claim 3 having the formula:

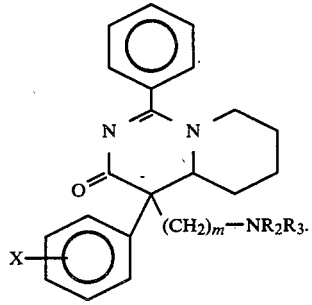

14. 2-phenyl-5-phenyl-5-[2-[N,N-bis(1-methylethyl)amino]ethyl]-1,3-diazabicyclo[4.4.0]dec-2-en-4-one, and the corresponding isomers and racemates thereof, compounds according to claim 13.

15. 2-phenyl-5-(4-phenylphenyl)-5-[2-[N,N-bis(1-methylethyl)amino]ethyl]-1,3-diazabicyclo[4.4.0]dec-2-en-4-one, and the corresponding isomers and racemates thereof, compounds according to claim 13.

16. 2-phenyl-5-(2-chlorophenyl)-5-[2-[N,N-bis(1-methylethyl)amino]ethyl]-1,3-diazabicyclo[4.4.0]dec-2-en-4-one, and the corresponding isomers and racemates thereof, compounds according to claim 13.

17. A compound according to claim 1 having the formula:

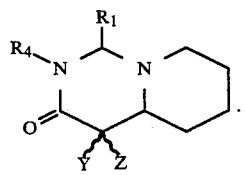

18. A compound according to claim 17 having the formula:

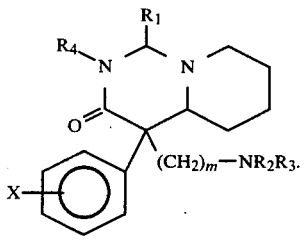

19. A compound according to claim 18 having the formula:

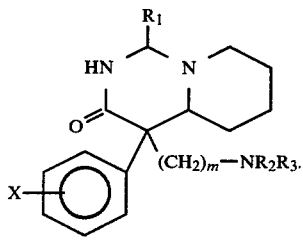

20. A compound according to claim 19 having the formula:

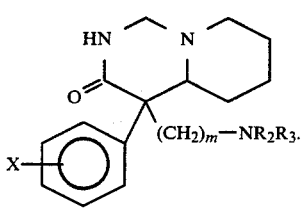

21. 5-phenyl-5-[2-[N,N-bis(1-methylethyl)amino]ethyl]-1,3-diazabicyclo[4.4.0]decan-4-one, and the corresponding isomers and racemates thereof, compounds according to claim 20.

22. 5-(4-phenylphenyl)-5-[2-[N,N-bis(1-methylethyl)amino]ethyl]-1,3-diazabicyclo[4.4.0]decan-4-one, and the corresponding isomers and racemates thereof, compounds according to claim 20.

23. 5-(2-chlorophenyl)-5-[2-[N,N-bis(1-methylethyl)amino]ethyl]-1,3-diazabicyclo[4.4.0]decan-4-one, and the corresponding isomers and racemates thereof, compounds according to claim 20.

24. A compound according to claim 19 having the formula:

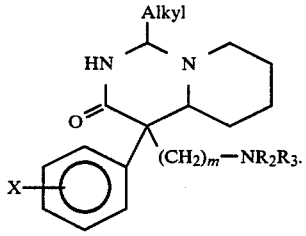

25. 2-methyl-5-phenyl-5-[2-[N,N-bis(1-methylethyl)amino]ethyl]-1,3-diazabicyclo[4.4.0]decan-4-one, and the corresponding isomers and racemates thereof, compounds according to claim 24.

26. 2-ethyl-5-phenyl-5-[2-[N,N-bis(1-methylethyl)amino]ethyl]-1,3-diazabicyclo[4.4.0]decan-4-one, and the corresponding isomers and racemates thereof, compounds according to claim 24.

27. 2-methyl-5-(4-phenylphenyl)-5-[2-[N,N-bis(1-methylethyl)amino]ethyl]-1,3-diazabicyclo[4.4.0]decan-4-one, and the corresponding isomers and racemates thereof, compounds according to claim 24.

28. 2-methyl-5-(2-chlorophenyl)-5-[2-[N,N-bis(1-methylethyl)amino]ethyl-1,3-diazabicyclo[4.4.0]decan-4-one, and the corresponding isomers and racemates thereof, compounds according to claim 24.

29. A compound according to claim 19 having the formula:

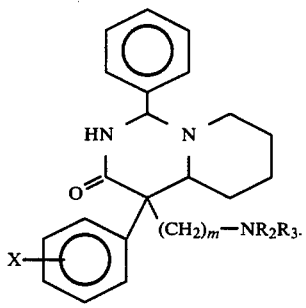

30. 2-phenyl-5-phenyl-5-[2-[N,N-bis(1-methylethyl)amino]ethyl]-1,3-diazabicyclo[4.4.0]decan-4-one, and the corresponding isomers and racemates thereof, compounds according to claim 29.

31. 2-phenyl-5-(4-phenylphenyl)-5-[2-[N,N-bis(1-methylethyl)amino]ethyl]-1,3-diazabicyclo[4.4.0]decan-4-one, and the corresponding isomers and racemates thereof, compounds according to claim 29.

32. 2-phenyl-5-(2-chlorophenyl)-5-[2-[N,N-bis(1-methylethyl)amino]ethyl]-1,3-diazabicyclo[4.4.0]decan-4-one, and the corresponding isomers and racemates thereof, compounds according to claim 29.

33. A compound according to claim 18 having the formula:

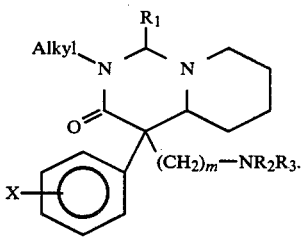

34. A compound according to claim 33 having the formula:

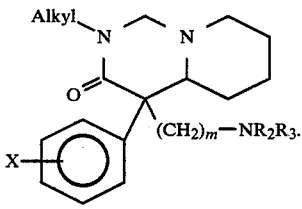

35. 3-methyl-5-phenyl-5-[2-[N,N-bis(1-methylethyl)amino]ethyl]-1,3-diazabicyclo[4.4.0]decan-4-one, and the corresponding isomers and racemates thereof, compounds according to claim 34.

* * * * *